(12) United States Patent
Hickey et al.

(10) Patent No.: US 8,980,597 B2
(45) Date of Patent: *Mar. 17, 2015

(54) FROM CARBON MONOXIDE AND HYDROGEN ANAEROBIC FERMENTATION PROCESSING USING A PRE-REACTOR/DEEP TANK REACTOR SYSTEM

(75) Inventors: Robert Hickey, Okemos, MI (US); Steven L. Donnellan, Park Ridge, IL (US)

(73) Assignee: Coskata, Inc., Warrenville, IL (US)

(*) Notice: Subject to any disclaimer, the term of this patent is extended or adjusted under 35 U.S.C. 154(b) by 373 days.

This patent is subject to a terminal disclaimer.

(21) Appl. No.: 13/243,347

(22) Filed: Sep. 23, 2011

(65) Prior Publication Data

US 2013/0078687 A1    Mar. 28, 2013

(51) Int. Cl.
  C12P 7/06    (2006.01)
  C12P 1/04    (2006.01)
  C12P 7/04    (2006.01)
  C12P 7/24    (2006.01)
  C12P 7/40    (2006.01)

(52) U.S. Cl.
  CPC ... *C12P 7/04* (2013.01); *C12P 7/24* (2013.01); *C12P 7/40* (2013.01); *Y02E 50/17* (2013.01)
  USPC .......................................... 435/161; 435/170

(58) Field of Classification Search
  None
  See application file for complete search history.

(56) References Cited

U.S. PATENT DOCUMENTS

| | | | |
|---|---|---|---|
| 4,162,970 A | 7/1979 | Zlokarnik et al. | |
| 4,426,450 A | 1/1984 | Donofrio | |
| 6,193,220 B1 | 2/2001 | Kelly | |
| 7,285,402 B2 | 10/2007 | Gaddy et al. | |
| 7,704,723 B2 | 4/2010 | Huhnke et al. | |
| 2003/0211585 A1 | 11/2003 | Gaddy et al. | |
| 2008/0305539 A1 | 12/2008 | Hickey et al. | |
| 2009/0215139 A1 | 8/2009 | Datta et al. | |
| 2011/0059499 A1 | 3/2011 | Simpson et al. | |

OTHER PUBLICATIONS

Datar et al., Biotechnol. Bioeng. 86(5): 587-594 (2004).*
Grethlein, "Metabolic engineering of product formation during carbon monoxide fermentation by Butyribacterium methylotrophicum", Ph.D. dissertation, Department of Chemical Engineering, Michigan State University, East Lansing, MI, 1991.*
U.S. Appl. No. 12/826,991, filed Jun. 30, 2010, Hickey et al.
Munasinghe, et al., Biomass-derived Syngas Fermentation in Biofuels: Opportunities and Challenges, Biosource Technology, 101 (2010) 5013-5022.
Munasinghe, et al., Syngas Fermentation to Biofuel: Evaluation of Carbon Monoxide Mass Transfer Coefficient (kLa) in Different Reactor Configurations, Biotechol. Prog., 2010.
Bredwell, et al., in Reactor Design Issues for Synthesis-Gas Fermentations, Biotechnol. Prog., 15 (1999) 834-844.

(Continued)

*Primary Examiner* — Patricia A Leith
*Assistant Examiner* — Erin M Bowers

(57) ABSTRACT

Processes are disclosed for the low energy, anaerobic bioconversion of hydrogen and carbon monoxide in a gaseous substrate stream to oxygenated organic compounds such as ethanol by contact with microorganisms in a fermentation system with high conversion efficiency of both hydrogen and carbon monoxide. The processes of this invention use a pre-reactor and a deep, tank reactor in gaseous substrate flow sequence to obtain high conversion of gas substrate without undue risk of carbon monoxide inhibition.

12 Claims, 1 Drawing Sheet

(56) References Cited

OTHER PUBLICATIONS

Xu, et al., The effects of syngas impurities on syngas fermentation to liquid fuels, Biomass and Bioenergy, 35, (2011), 2690-2696.

Krishna, et al., Influence of alcohol addition on gas hold-up in bubble columns: development of a scale up model, Int. Comm. Heat Mass Transfer, 27 No. 4, (2000) 465-472.

Wilkins, et al., Microbial productoin of ethanol from carbon monoxide, Current Opinion in Biotechnology, 22 (2011), 326-330.

Ahmed, et al., Fermentation of Biomass-Generated Synthesis Gas: Effects of Nitric Oxide, Biotechnology and Bioengineering, 97, No. 5, (2007), 1080-1086.

Abubackar, et al., Biological conversion of carbon monoxide: rich syngas or waste gas to bioethanol, Biofuels, Bioproducts & Biorefining, 5 (2011), 93-114.

* cited by examiner

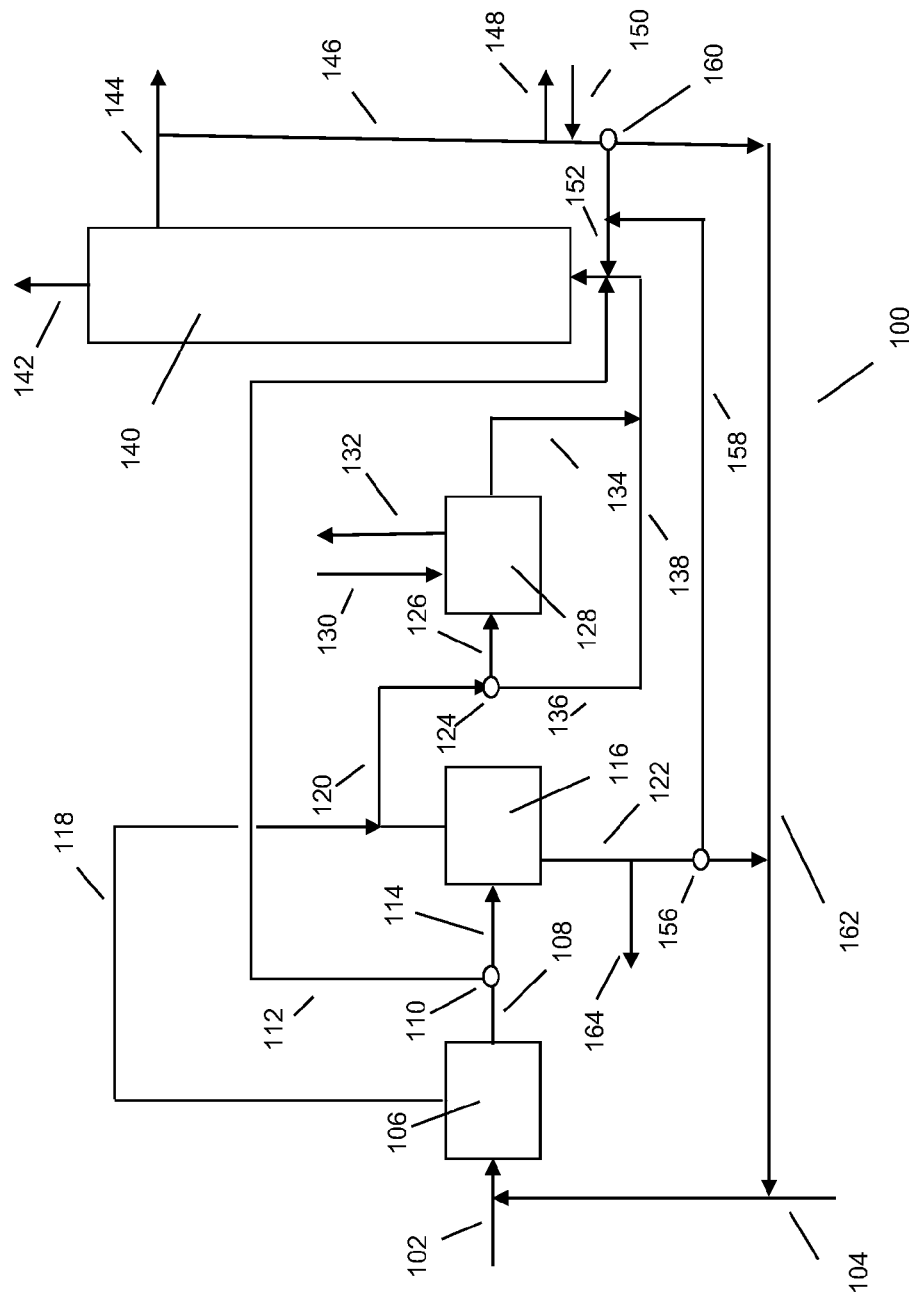

FROM CARBON MONOXIDE AND HYDROGEN ANAEROBIC FERMENTATION PROCESSING USING A PRE-REACTOR/DEEP TANK REACTOR SYSTEM

FIELD OF THE INVENTION

This invention pertains to processes for the low energy, anaerobic bioconversion of hydrogen and carbon monoxide in a gaseous substrate stream to oxygenated organic compounds such as ethanol by contact with microorganisms in a fermentation system with high conversion efficiency of both hydrogen and carbon monoxide. The processes of this invention use a pre-reactor and a deep, tank reactor in gaseous substrate flow sequence to obtain high conversion of gas substrate without undue risk of carbon monoxide inhibition.

BACKGROUND

Anaerobic fermentations of hydrogen and carbon monoxide involve the contact of the substrate gas in a liquid aqueous menstruum with microorganisms capable of generating oxygenated organic compounds such as ethanol, acetic acid, propanol and n-butanol. The production of these oxygenated organic compounds requires significant amounts of hydrogen and carbon monoxide. For instance, the theoretical equations for the conversion of carbon monoxide and hydrogen to ethanol are:

$$6CO + 3H_2O \rightarrow C_2H_5OH + 4CO_2$$

$$6H_2 + 2CO_2 \rightarrow C_2H_5OH + 3H_2O.$$

As can be seen, the conversion of carbon monoxide results in the generation of carbon dioxide. The conversion of hydrogen involves the consumption of hydrogen and carbon dioxide, and this conversion is sometimes referred to as the $H_2/CO_2$ conversion. For purposes herein, it is referred to as the hydrogen conversion.

Typically the substrate gas for carbon monoxide and hydrogen conversions is or is derived from a synthesis gas (syngas) from the gasification of carbonaceous materials, reforming of natural gas and/or biogas from anaerobic fermentors or from off streams of various industrial methods. The gas substrate contains carbon monoxide, hydrogen, and carbon dioxide and usually contains other components such as water vapor, nitrogen, methane, ammonia, hydrogen sulfide and the like. (For purposes herein, all gas compositions are reported on a dry basis unless otherwise stated or clear from the context.)

Syngas fermentation processes suffer from the poor solubility of the gas substrate, i.e., carbon dioxide and hydrogen, in the liquid phase of the aqueous menstruum. Munasinghe, et al., in *Biomass-derived Syngas Fermentation in Biofuels: Opportunities and Challenges, Biosource Technology,* 101 (2010) 5013-5022, summarize volumetric mass transfer coefficients to fermentation media reported in the literature for syngas and carbon monoxide in various reactor configurations and hydrodynamic conditions. A number of conditions can enhance the mass transfer of syngas to the liquid phase. For instance, increasing the interfacial area between the gas feed and the liquid phase can improve mass transfer rates.

Numerous processes have been disclosed for the conversion of carbon monoxide and hydrogen to oxygenated compounds. One such process suspends the microorganisms for the conversion in an aqueous menstruum contained in a stirred tank reactor such as by using a motor driven impeller. Stirred tank fermentation reactors provide many advantages. For stirred tank reactors, increasing the agitation of the impeller is said to improve mass transfer as smaller bubble sizes are obtained. Also, the stirring action not only distributes the gas phase in the aqueous menstruum but also the duration of the contact between the phases can be controlled. Another very significant benefit is that the composition within the stirred tank can be relatively uniform. For instance, Munasignhe, et al., in a later published paper, *Syngas Fermentation to Biofuel: Evaluation of Carbon Monoxide Mass Transfer Coefficient ($k_La$) in Different Reactor Configurations, Biotechol. Prog.,* 2010, Vol. 26, No. 6, pp 1616-1621, combine a sparger (0.5 millimeter diameter pores) with mechanical mixing at various rotational rates to provide enhanced mass transfer. This uniformity enables good control of the fermentation process during steady-state operation. This is of particular advantage in the anaerobic conversion of carbon monoxide and hydrogen to oxygenated compounds where two conversion pathways exist. Hence the carbon dioxide generated from the conversion of carbon monoxide is proximate in location to the hydrogen consumption pathway that consumes carbon dioxide. The uniformity further facilitates the addition of fresh gas substrate. The problems with stirred tank reactors are capital costs, the significant amount of energy consumed in the needed mixing and agitation, and the need for plural stages to achieve high conversion of substrate.

Bredwell, et al., in *Reactor Design Issues for Synthesis-Gas Fermentations,* Biotechnol. Prog., 15 (1999) 834-844, assessed various types of reactors including bubble columns and stirred reactors. The authors disclose using microbubble sparging with mechanical agitation. At page 839 they state:

"When microbubble sparging is used, only enough power must be applied to the reactor to provide adequate liquid mixing. Thus axial flow impellers desinged to have low shear and a high pumping capacity would be suitable when microbubbles are used in stirred tanks."

They conclude by stating:

"An improved ability to predict and control coalescence rates is needed to rationally design commercial-scale bioreactors that employ microbubble sparging."

Another type of fermentation apparatus is a bubble column fermentation reactor wherein the substrate gas is introduced at the bottom of the vessel and bubbles through the aqueous menstruum ("bubble reactor"). See Munasinghe, et al., in *Biomass-derived Syngas Fermentation in Biofuels: Opportunities and Challenges, Biosource Technology,* 101 (2010) 5013-5022. In order to achieve sought mass transfer from the gas to liquid phases, workers have provided the gas feed to bubble columns in the form of microbubbles. The authors report that in one study, the mass transfer obtained for a bubble column reactor was higher than that for a stirred tank reactor mainly due to the higher interfacial surface area obtained with the bubble column reactor. Advantageously, commercial-scale bubble column fermentation reactors are relatively simple in design and construction and require relatively little energy to operate.

In co-pending U.S. patent application Ser. No. 13/243,426, filed on even date herewith, processes are disclosed for enhancing the performance of large-scale, anaerobic fermentors. In these processes, a reactor having an aqueous menstruum depth of at least about 10 meters is used, and gas feed is supplied to the aqueous menstruum in the form of a stable gas-in-liquid dispersion. The aqueous menstruum is mechanically stirred at a rate sufficient to provide relatively uniform liquid phase composition within the aqueous menstruum without unduly adversely affecting the gas-in-liquid dispersion. For purposes herein the type of stirred tank reactor used in the processes of this invention is called a mechanically-assisted liquid distribution tank reactor, or MLD tank reactor. With the relatively uniform composition throughout the MLD tank reactor provided by the mechanical stirring, regardless of where the gas feed is introduced, bubbles will be moved throughout the volume of the aqueous menstruum. At least a portion of the off-gas from the aqueous menstruum is recycled to obtain a conversion efficiency of total hydrogen and carbon monoxide in the gas substrate to oxygenated organic compound of at least about 80 mole percent in a single reactor stage. Accordingly, capital cost savings and energy savings can be achieved using a MLD tank reactor as compared to a conventional stirred tank reactor.

For purposes herein, both deep, bubble column fermentation reactors and the large-scale liquid mixing reactors supplied with stable gas feed-in-liquid dispersions and using low stirring rates, are referred to as deep, tank reactors.

Deep, tank reactors using microbubbles can provide economically attractive facilities for anaerobic conversion of syngas to oxygenated organic compound, but difficulties are present. In their earlier review article, Munasignhe, et al., report that the gas-liquid mass transfer is the major resistance for gaseous substrate diffusion. The authors state at page 5017:

"High pressure operation improves the solubility of the gas in the aqueous phase. However, at higher concentrations of gaseous substrates, especially CO, anaerobic microorganisms are inhibited."

Other workers have understood that the presence of excess carbon monoxide can adversely affect the microorganisms and their performance. See paragraphs 0075 through 0077 and 0085 though 0086 of United States published patent application No. 20030211585 (Gaddy, et al.) disclosing a continuously stirred tank bioreactor for the production of ethanol from microbial fermentation. At paragraph 0077, Gaddy, et al., state:

"The presence of excess CO unfortunately also results in poor $H_2$ conversion, which may not be economically favorable. The consequence of extended operation under substrate inhibition is poor $H_2$ uptake. This eventually causes cell lysis and necessary restarting of the reactor. Where this method has an unintended result of CO substrate inhibition (the presence of too much CO for the available cells) during the initial growth of the culture or thereafter, the gas feed rate and/or agitation rate is reduced until the substrate inhibition is relieved."

At paragraph 0085, Gaddy, et al., discuss supplying excess carbon monoxide and hydrogen. They state:

"A slight excess of CO and $H_2$ is achieved by attaining steady operation and then gradually increasing the gas feed rate and/or agitation rate (10% or less increments) until the CO and $H_2$ conversions just start to decline."

For deep, tank reactors, the height of the aqueous menstruum is a primary determinant of the contact time for the bioconversion to occur. This height also is a determinant of the static head at the bottom portion of the reactor. Higher pressures result in smaller bubble sizes and higher partial pressures both of which enhance mass transfer efficiency and gas substrate conversion efficiency in the fermentation reactor. Thus, on a commercial scale, deep, tank reactors have a depth of at least about 10, preferably at least about 15, meters and use microbubbles of gas feed in order to achieve conversion efficiencies of at least about 60 percent of the total moles of hydrogen and carbon monoxide supplied to the reactor. However, these operating parameters increase the risk of carbon monoxide inhibition.

For a syngas to oxygenated organic compound fermentation process to be commercially viable, capital and operating costs must be sufficiently low that it is at least competitive with alternative biomass to oxygenated organic compound processes. For instance, ethanol is commercially produced from corn in facilities having name plate capacities of over 100 million gallons per year. Accordingly, the syngas to oxygenated organic compound fermentation process must be able to take advantage of similar economies of scale. Thus, a commercial scale facility may require at least 20 million liters of fermentation reactor capacity. Deep, tank reactors, i.e., reactors having heights of at least 10 meters such as bubble column reactors and mechanically-mixed tank reactors, are attractive for commercial operations due to their large volumes and low capital costs. As reported by Munasignhe, et al., syngas fermentation reactor types such a bubble column reactors and air lift (jet loop) reactors are less costly to manufacture and operate yet can provide good mass transfer rates of syngas to the liquid phase.

In addition to economies of scale, the processes need to obtain high conversion efficiencies of the syngas to oxygenated organic compounds. Syngas and other carbon monoxide and hydrogen-containing gas feeds are typically more expensive than equivalent heat content amounts of fossil fuels. Hence, a desire exists to use these gases effectively to make higher value products. The financial viability of any conversion process, especially to commodity chemicals such as ethanol and acetic acid, will be dependent upon the efficiency of conversion efficiency of the carbon monoxide and hydrogen, the conversion selectivity to the sought products and the energy costs to effect the conversion.

The gas feed can be introduced at the bottom of a deep, tank reactor where the most favorable conditions for mass transfer of carbon monoxide from the gas to the liquid phase exist. Hence, to avoid carbon monoxide inhibition, operating parameters such as carbon monoxide mole fraction in the gas feed, gas feed supply rate and microbubble size must be controlled to assure that the carbon monoxide mass transfer rate does not become so great as to cause carbon monoxide inhibition. However, the conditions required to avoid carbon monoxide inhibition in a deep, tank reactor negatively affect the overall amount of carbon monoxide that can be transferred to the liquid phase, and thus the conversion efficiency to oxygenated organic compound.

This negative effect is particularly exacerbated for deep, bubble column reactors since the static pressure is reduced as the microbubbles pass upwardly, the partial pressure of carbon monoxide in the bubbles decreases and the surface area to volume of the microbubbles may decrease. Furthermore, the compositions of the gas and liquid phases change over the height of the aqueous menstruum, further negatively affecting mass transfer of hydrogen and carbon monoxide to the liquid phase. Carbon dioxide co-product is generated by the carbon monoxide pathway and the solubility of carbon dioxide in the aqueous menstruum is highly sensitive to pressure. Thus, at higher elevations of the aqueous menstruum, carbon dioxide can pass to the bubbles and reduce the mole fractions of hydrogen and carbon monoxide in the gas phase. The reduced mole fractions also reduce the driving force for mass transfer of carbon monoxide and hydrogen to the liquid phase.

The net result is that conversion efficiencies, especially for hydrogen, in a deep, tank reactor are often low. Increasing the depth to provide a longer contact time provides ever diminishing benefits, increases the risk of carbon monoxide inhibition and thus is not a solution by itself to obtain sought high bioconversion efficiencies.

Accordingly, processes are sought that can take advantage of the benefits of deep, tank reactors using small bubbles without undue risk of carbon monoxide inhibition.

SUMMARY

By this invention, deep fermentation reactors are able to achieve high bioconversion of gas substrate comprising carbon monoxide and hydrogen to oxygenated organic compound by anaerobic fermentation in an aqueous menstruum without undue energy costs and without undue risk of carbon monoxide inhibition. The processes of this invention prereact the gas feed to a deep, tank reactor which has a sufficient depth of aqueous menstruum and is operated using microbubbles of gas feed to enhance conversion of carbon monoxide and hydrogen without undue risk of carbon monoxide inhibition. The deep, tank reactor has a height of at least about 10, often between about 10 or 15 and 30, meters and an aspect ratio of height to diameter of at least about 0.5:1, say, between about 0.5:1 to 5:1, preferably between about 1:1 to 3:1, The microbubbles of gas feed introduced into the aqueous menstruum are generated by injection of the gas feed with a motive liquid. In preferred processes, the gas feed is injected into the deep, tank reactor as a relatively stable gas-in-water dispersion.

By using a deep, tank reactor, a static head will occur at the lower portion that increases the partial pressure of the gas in the microbubbles and reduces bubble sizes, both of which serve to increase mass transfer rates to the liquid phase and the ability to achieve high conversions. In accordance with the processes of this invention, the gas feed is subjected to a pre-reaction to reduce the mole fraction of carbon monoxide in the feed prior to being supplied to the deep, tank reactor. The pre-reaction converts less than about 40 percent of the carbon monoxide. However, as carbon dioxide is a co-product of the carbon monoxide conversion to oxygenated organic product, the mole fraction of the carbon monoxide in the gas feed is further reduced. Thus, the mass transfer rate of carbon monoxide from the microbubbles to the liquid phase of the aqueous menstruum in the deep, tank reactor is reduced and with such a reduction, the risk of carbon monoxide inhibition is diminished. Yet, the deep, tank reactor is able, with the presence of microbubbles providing enhanced mass transfer rates and higher gas residence times in the deep, tank reactor, to achieve high conversions of the gas substrate. The total, overall molar conversion of carbon monoxide and hydrogen in the gas substrate to oxygenated organic compound is at least about 80, preferably at least about 85, often between about 85 and 95, percent.

In one broad aspect, the processes of this invention comprise the continuous process for the anaerobic bioconversion of a gas substrate comprising carbon monoxide, carbon dioxide and hydrogen in an aqueous menstruum containing microorganisms suitable for converting said substrate to oxygenated organic compound, said process comprising:

a. continuously supplying a gas feed comprising said gas substrate to a pre-reactor assembly comprising at least one pre-reactor for contact with an aqueous menstruum therein, said contacting being under fermentation conditions sufficient to convert in the pre-reactor assembly between about 10 and 40 percent of carbon monoxide in the gas feed to said oxygenated organic compound and provide a pretreated gas comprising unreacted carbon monoxide in a mole fraction less than that in the gas feed, unreacted hydrogen, and carbon dioxide in a mole fraction greater than that in the gas feed;

b. continuously supplying at least a portion of the pretreated gas to a deep, tank reactor as microbubbles having a diameter of less than about 500, say, about 10 or 20 to 300, microns for contact with an aqueous menstruum therein, said contacting being under fermentation conditions sufficient to provide a total, overall molar conversion of carbon monoxide and hydrogen contained in said gas feed in steps a and b to said oxygenated organic compound of at least about 80 percent; and c. recovering oxygenated organic compound from the aqueous menstruum from the deep, tank reactor.

Another broad embodiment of the invention pertains to processes for the production of oxygenated organic compound from gas feed comprising carbon monoxide, hydrogen and carbon dioxide by anaerobic fermentation in an aqueous menstruum under fermentation conditions, said liquid menstruum containing microorganism suitable for such production, using a deep fermentation reactor containing aqueous menstruum having a depth of at least 10 meters, the improvement comprising:

a. contacting the gas feed with aqueous menstruum in a pre-reactor assembly prior to being contacted with aqueous menstruum in the deep, tank reactor, said contacting in the pre-reactor assembly being under fermentation conditions and time sufficient to provide a pretreated gas to the deep, tank reactor that contains between about 5 and 30, often between about 10 and 20, mole percent carbon monoxide; and b. supplying the gas feed to the deep, tank reactor as microbubbles having a diameter of less than about 100 microns.

The deep, tank reactor may be of any suitable configuration, including but not limited to bubble column reactors, jet loop reactors and stirred tank reactors. These types of reactors provide for microbubbles to be dispersed throughout, thereby taking advantage of the static head. While bubble column reactors are typically the most economical design and can provide high conversion efficiencies, other reactor designs may find utility in commercially viable bioconversion facilities. Where stirred tank reactors are used, they preferably are MLD reactors where the stirring is insufficient to generate small bubbles.

The microbubbles are preferably generated by using a motive fluid injector for instance in a venturi or jet injector, rather than mechanical stirring thereby realizing energy savings. Moreover, the injectors can provide better control over the size of the microbubbles produced. As the size of the microbubbles can be varied by changing the rate of flow of the motive liquid, an additional means for control of the mass transfer of gas substrate to the liquid phase can be achieved. Additionally, the modulation enables a microbubble size to be generated that results in a preferred, stable gas-in-water dispersion. Jet injectors, and especially slot injectors, can provide a suitable sized bubble to enable the stable dispersion to be formed while maintaining a surface area to volume ratio to provide a rate of transfer high enough to obtain desired efficiencies of conversion but low enough to avoid carbon monoxide inhibition.

In a preferred embodiment, the pre-reactor system serves to provide microorganisms to the deep, tank reactor and thus maintain the culture in the deep, tank reactor to enhance gas substrate conversion efficiencies. In this embodiment, at least a portion of the aqueous menstruum is passed from a pre-reactor to the deep, tank reactor. The liquid residence time in the pre-reactor is often between about 15 and 50 hours. If desired, aqueous menstruum may be withdrawn from the pre-reactor assembly for recovery of oxygenated organic compound and solids purge. Alternatively and preferably, the rate that aqueous menstruum is passed to the deep, tank reactor may be sufficient that no withdrawal of aqueous menstruum is required for product recovery and solids purge from the pre-reactor.

The aqueous menstruum being passed to the deep, tank reactor from the pre-reactor assembly contains gas bubbles that may or may not be of the size sought for use in the deep, tank reactor. If desired, at least a portion of the gas bubbles can be removed from this aqueous menstruum stream and that gas combined with the treated gas for supply as microbubbles to the deep, tank reactor. Any suitable gas removal operation can be used including, but not limited to, allowing the bubble to rise and escape from the aqueous menstruum in a degassing tank, using vane separators, and using centrifugal devices including centrifuges and hydrocyclones. Where the pre-reactor system is used to supply microorganisms to the deep, tank reactor, preferably between about 10 to 40, say 25 to 40, percent of the carbon monoxide in the gas feed is bioconverted in the pre-reactor.

BRIEF DESCRIPTION OF THE DRAWING

FIG. 1 is a schematic flow diagram of a pre-reactor assembly and a deep, MLD tank reactor adapted to use the process of this invention.

DETAILED DISCUSSION

Definitions

Oxygenated organic compound means one or more organic compounds containing two to six carbon atoms selected from the group of aliphatic carboxylic acids and salts, alkanols and alkoxide salts, and aldehydes. Often oxygenated organic compound is a mixture of organic compounds produced by the microorganisms contained in the aqueous menstruum.

Carbon monoxide inhibition means that microorganisms are adversely affected by a high concentration of dissolved carbon monoxide in the aqueous menstruum resulting in a significantly reduced, e.g., reduced by at least 15 percent, conversion of carbon monoxide or hydrogen per gram of active cells per liter, all other conditions remaining the same. The inhibitory effect may occur in a localized region in the aqueous menstruum; however, the occurrence of a carbon monoxide inhibition is typically observed by assessing the specific activity rate, i.e., the mass bioconsumed per mass of active microorganism per unit time, which under steady-state conditions can be approximated by the overall conversion for the volume of aqueous menstruum in the reactor. The concentration of carbon monoxide dissolved in the aqueous menstruum that results in carbon monoxide inhibition varies depending upon the strain of microorganism and the fermentation conditions.

Aqueous menstruum means a liquid water phase which may contain dissolved compounds including, but not limited to hydrogen, carbon monoxide, and carbon dioxide.

The motive liquid may be any suitable liquid for introduction into the reactor. The motive liquid comprises sufficient amount of one or more of oxygenated organic compound and other surface active agent to enhance the formation of microbubbles.

Microbubbles are bubbles having a diameter of 500 microns or less.

The pressure at the point of injection into the aqueous menstruum is the sum of the absolute pressure at the point calculated as if the liquid head above such point were water. The partial pressure of a gas feed component is determined as the product of the mole fraction of a component in a gas mixture times the total pressure. The partial pressure of a component in the gas being fed to a reaction reactor is calculated as the mole fraction of that component times the pressure in the reaction reactor at the point of entry.

Stable gas-in-liquid dispersion means a mixture of gas bubbles in liquid where (i) the bubbles predominantly flow in the same direction as the liquid, and (ii) the dispersion is sufficiently stable that it exists throughout the aqueous menstruum, i.e., insufficient coalescing of bubbles occurs to destroy the dispersion.

Overview

The processes of this invention pertain to operating deep, tank reactors for anaerobic conversion of gas substrate containing carbon monoxide, hydrogen and carbon dioxide to obtain high conversion efficiencies to oxygenated organic compound such as ethanol, acetic acid, propanol, propionic acid, butanol and butyric acid while avoiding carbon monoxide inhibition by pre-reacting the gas feed.

Substrate and Feed Gas:

Anaerobic fermentation to produce oxygenated organic compound uses a substrate comprising carbon monoxide, carbon dioxide and hydrogen, the later being for the hydrogen conversion pathway. The gas feed will typically contain nitrogen and methane in addition to carbon monoxide and hydrogen. Syngas is one source of a gas substrate. Syngas can be made from many carbonaceous feedstocks. These include sources of hydrocarbons such as natural gas, biogas, biomass, especially woody biomass, gas generated by reforming hydrocarbon-containing materials, peat, petroleum coke, coal, waste material such as debris from construction and demolition, municipal solid waste, and landfill gas. Syngas is typically produced by a gasifier. Any of the aforementioned biomass sources are suitable for producing syngas. The syngas produced thereby will typically contain from 10 to 60 mole % CO, from 10 to 25 mole % $CO_2$ and from 10 to 60 mole % $H_2$. The syngas may also contain $N_2$ and $CH_4$ as well as trace components such as $H_2S$, COS, $NH_3$ and HCN. Other sources of the gas substrate include gases generated during petroleum and petrochemical processing. These gases may have substantially different compositions than typical syngas, and may be essentially pure hydrogen or essentially pure carbon monoxide. The gas substrate may be obtained directly from gasification or from petroleum and petrochemical processing or may be obtained by blending two or more streams. Also, the gas substrate may be treated to remove or alter the composition including, but not limited to, removing components by chemical or physical sorption, membrane separation, and selective reaction. Components may be added to the gas substrate such as nitrogen or adjuvant gases such as ammonia and hydrogen sulfide.

For the sake of ease of reading, the term syngas will be used herein and will be intended to include these other gas substrates.

Oxygenated Compounds and Microorganisms:

The oxygenated organic compounds produced in the processes of this invention will depend upon the microorganism used for the fermentation and the conditions of the fermentation. Bioconversions of CO and $H_2/CO_2$ to acetic acid, n-butanol, butyric acid, ethanol and other products are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds, Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogemum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA-10522 filed as U.S. Ser. No. 12/272,320 on Mar. 19, 2010. All of these references are incorporated herein in their entirety.

Aqueous Menstruum and Fermentation Conditions:

The aqueous menstruum for both the pre-reactor and deep, tank reactor will comprise an aqueous suspension of microorganisms and various media supplements. The aqueous menstruum for the primary reactor may be substantially the same or may be different from the aqueous menstruum for the sequential reactor. The fermentation conditions for the primary and for the secondary reactors may be substantially the same or different.

Suitable microorganisms generally live and grow under anaerobic conditions, meaning that dissolved oxygen is essentially absent from the fermentation liquid. The various adjuvants to the aqueous menstruum may comprise buffering agents, trace metals, vitamins, salts etc. Adjustments in the menstruum may induce different conditions at different times such as growth and non-growth conditions which will affect the productivity of the microorganisms. Previously referenced U.S. Pat. No. 7,704,723 discloses the conditions and contents of suitable aqueous menstruum for bioconversion CO and $H_2/CO_2$ using anaerobic microorganisms.

The aqueous menstruum in both the pre-reactor and deep, tank reactor is maintained under anaerobic fermentation conditions including a suitable temperature, say, between 25 C and 60 C, frequently in the range of about 3° C. to 40 C. The conditions of fermentation, including the density of microorganisms and aqueous menstruum composition, are preferably sufficient to achieve the sought conversion of hydrogen and carbon monoxide in each of the pre-reactor and deep, tank reactor.

The top of the pre-reactor and the deep, tank reactor may be under pressure, at atmospheric pressure, or below ambient pressure.

The average residence time of the gas in the aqueous menstruum of the deep, tank reactor will depend upon the depth of the aqueous menstruum; the size of the microbubbles; and the internal fluid flows in the reactor including the type of deep, tank reactor. While baffles or other flow-directing devices can be used, they are not essential to this invention. In general, the average residence time is between about 50 and 1000, say 100 and 300, seconds. The average residence time of the gas in the aqueous menstruum of the pre-reactor will depend upon the depth of the aqueous menstruum; the size of the microbubbles; and the internal fluid flows in the reactor including the type of pre-reactor. While baffles or other flow-directing devices can be used, they are not essential to this invention. In general, the average residence time in the pre-reactor is between about 20 and 500, say 30 and 200, seconds.

Any suitable procedure may be used to start-up a deep, tank reactor and a pre-reactor. Typically, the reactor is filled with a gas not containing reactive oxygen. Although a wide variety of gases for blanketing can be used, such as gases containing carbon dioxide, nitrogen or lower alkane, e.g., alkane of 1 to 3 carbon atoms such as methane and natural gas, cost and availability considerations play a role in the selection of the blanketing gas as well as its acceptability to the anaerobic fermentation process and subsequent unit operations. For large volume reactors, typically the reactor is partially charged with aqueous menstruum containing microorganisms and gas feed is provided to grow the culture of microorganisms and additional aqueous menstruum is provided until the aqueous menstruum has obtained the desired height in the reactor and the density of microorganisms has reached its desired level. Start-up procedures for deep, tank reactors are disclosed in co-pending United States patent application Ser. No. 13/243,159, filed on even date herewith and incorporated by reference in its entirety.

Deep, Tank Reactor and its Operation

The deep, tank reactor is of a sufficient volume that the fermentation process is commercially viable. Preferably the reactors are designed to contain at least 1 million, and more preferable at least about 5, say about 5 to 25 million, liters of aqueous menstruum. In order to accommodate such high volumes of aqueous menstruum, deep, tank reactors are used. These reactors are characterized as having a height of at least about 10, often between about 10 or 15 and 30, meters and an aspect ratio of height to diameter of at least about 0.5:1, say, 0.5:1 to 5:1, preferably between about 0.75:1 to 3:1. While the reactors are typically circular in cross-section, other cross-sectional configurations can be used provided that uniformity in the liquid phase is obtained. As the fermentation is anaerobic, the fermentation reactor must be sealed and not contain deleterious amounts of oxygen, usually less than 200, preferably less than about 100, parts per million by volume.

The deep, tank reactor may be a liquid mixed reactor or preferably a bubble column reactor. Bubble column reactors may contain axial-flow promoting devices such as baffles, down draft tubes and the like although these devices add to the capital costs of the reactors. Hence, most bubble column reactors do not contain these devices.

Liquid mixed reactors use one or more mechanical stirrers. The mechanical stirring should be sufficient to promote the uniformity of liquid composition through the reactor and need not, and preferably is not, used as a generator of a significant fraction of the microbubbles. Usually two or more mechanical stirrers are used at different heights with higher aspect ratio reactors. The design of mechanical stirrers for stirred tank reactors and their positioning within the reactors for very large diameter tanks are well within the skill of a stirred tank reactor designer. Side paddles or side mounted mixers with impellers are frequently used. Axial flow impellers are sometimes used for deep, tanks less than about 5 or 7 meters in diameter. Preferably the design of the mechanical stirrers and the positioning within the reactor take into consideration energy costs in generating the liquid flow to obtain uniformity of the aqueous menstruum in the reactor.

By using a motive fluid in an injector to generate the microbubbles for the dispersion, rather than the mechanical stirring, energy savings are realized. Moreover, the injectors can provide better control over the size of the microbubbles. The mechanical stirring is preferably not so robust as to cause undue damage to the microorganisms, yet is still sufficient to achieve the desired uniformity of liquid phase throughout the reactor. A liquid mixed reactor may contain baffles or other static flow directing devices.

If a jet loop reactor is used as the deep, tank reactor, one or more vertical tubes may be used in the deep, tank reactor. It is not essential that these tubes extend the entire height of the aqueous menstruum. Positioning of treated gas injectors can be used to direct the flow around the loop. Preferably, the gas injectors are positioned at the top of a tube to direct the aqueous menstruum and microbubble dispersion downwardly. Thus, the initial static head, and the driving force for mass transfer of carbon monoxide into the liquid phase, is lower than that if the gas feed were introduced at a bottom portion of the deep, tank reactor.

Gas Feed Supply and Microbubbles and their Generation

The rate of supply of the gas feed under steady state conditions to each of the pre-reactor and deep, tank reactor is such that the rate of transfer of carbon monoxide and hydrogen to the liquid phase matches the rate that carbon monoxide and hydrogen are bioconverted. Hence, the dissolved concentration of carbon monoxide and hydrogen in the aqueous phase remains constant, i.e., does not build-up. The rate at which carbon monoxide and hydrogen can be consumed will be affected by the nature of the microorganism, the concentration of the microorganism in the aqueous menstruum and the fermentation conditions. As the rate of transfer of carbon monoxide and hydrogen to the aqueous menstruum is a parameter for operation, conditions affecting the rate of transfer such as interfacial surface area between the gas and liquid phases and driving forces are important. For instance, at a given flow rate of gas feed having a given composition to a reactor, the rate of transfer of carbon monoxide and hydrogen can vary widely depending upon the size of the microbubbles and upon the pressure.

The gas feed may be provided to the pre-reactor in any suitable manner. Often the gas feed is supplied by sparging, venturi nozzles or injection with a motive liquid. Depending upon the sought carbon monoxide conversion efficiency for the pre-reactor, bubble sizes larger than microbubbles may be acceptable, e.g., the bubble sizes may range up to 2 or 3 millimeters in diameter. However, in many instances it may be desirable to provide the gas feed in the form of microbubbles and have a stable gas-in-liquid dispersion in the pre-reactor.

The gas feed is provided as microbubbles to the deep, tank reactor by injection using a motive fluid. Where injection is used, variations in the motive liquid flow rate can be used to modulate the microbubble size and thus modulate the rate of transfer of carbon monoxide and hydrogen to the liquid phase.

The processes of this invention use microbubbles of pretreated gas feed in the deep, tank reactor. Preferably the reactor contains 2 or more injectors, and commercial scale reactors will often contain at least 2, often 4 to 8 or 10, laterals of injectors with as many as 100 or more injectors. The number of injectors used is typically selected based upon the ability to be able to transfer adequate amounts of gas substrate under steady-state operating conditions and to enhance cross-sectional uniformity of the gas phase in the reactor.

The injectors may be jet mixers/aerators or slot injectors. Slot injectors are preferred, one form of which is disclosed in U.S. Pat. No. 4,162,970. These injectors operate using a motive liquid. The injectors, especially slot injectors, are capable of operating over a wide range of liquid and gas flow rates and thus are capable of significant turn down in gas transfer capability. The injectors are characterized as having nozzles of at least about 1, often about 1.5 to 5, say, 2 to 4, centimeters as the cross-sectional dimension in the case of jet injectors or as the smaller cross-sectional dimension in the case of slot injectors. The large cross-sectional dimension of the injectors provides several benefits in addition to being able to produce microbubbles. First, they are not prone to fouling including where aqueous menstruum is used as the motive liquid as would be a sparger designed to produce microbubbles. Second, where the aqueous menstruum is used as the motive fluid, high momentum impact of the microorganisms with solid surfaces is minimized thereby minimizing the risk of damage to the microorganisms. Third, the energy required to provide microbubbles of a given size is often less than that required to form microbubbles of that size using a microbubble sparger. Fourth, a high turn down ratio can be achieved. And fifth, the microbubble size can be easily varied over a wide range.

The bubble size generated by the injectors will be influenced by, among other factors, the rate of liquid flow through the injector and the ratio of gas phase to liquid phase passing through the injector as well as characteristics of the aqueous menstruum itself including, but not limited to its static liquid depth. Consequently, an injector can be operated to provide a selected bubble size which enhances the ability to use the injector in a modulation mode, i.e., provide the adjustment in the rate of transfer of carbon monoxide to the liquid phase based upon the size of the culture and its ability of the culture to bioconvert the carbon monoxide. The modulation can also be used to obtain, if desired, a stable gas-in liquid dispersion. The modulation can be obtained by changing one or more of (i) the gas to liquid flow ratio to the injector thus changing the volume of gas feed and (ii) changing the rate of motive liquid and thus the bubble size which affects the rate of transfer of carbon monoxide from the gas phase to liquid phase. Additionally, modulation can be obtained by changing the gas feed composition and thus the mole fraction of carbon monoxide in the gas feed.

Preferably the gas feed is introduced by the injector into the menstruum in the form of microbubbles having diameters in the range of 0.01 to 0.5, preferably 0.02 to 0.3 millimeter. At start-up and where desired, larger bubble sizes, in the range of 100 to 5000 microns in diameter may be used. Also a portion of the gas feed may be introduced by sparging to generate large bubbles, say, 1 to 5 or 10, millimeters in diameter, for assisting in mixing the aqueous menstruum. The gas substrate may be introduced into the bottom portion of the deep, bubble column reactor as a gas stream or as a gas in liquid dispersion as disclosed in U.S. patent application Ser. No. 12/826,991, filed Jun. 30, 2010. The presence of the oxygenated organic compound and/or other surface active agent enhances the formation of fine microbubbles.

The motive liquid may be any suitable liquid for introduction into the reactor. Advantageously, the motive liquid is one or more of aqueous menstruum, liquid derived from aqueous menstruum or make-up liquid to replace aqueous menstruum withdrawn from product recovery. Preferably the motive liquid comprises aqueous menstruum.

The flow rate of motive liquid used in an injector will depend upon the type, size and configuration of the injector and the sought bubble size of the gas feed. In general, the velocity of the dispersion stream leaving the injector is frequently in the range of 0.5 to 5 meters per second and the ratio of gas to motive liquid is in the range of from about 1:1 to 3:1 actual cubic meters per cubic meter of motive liquid.

The microbubbles form a stable gas-in-water dispersion. The introduction of the microbubbles into the aqueous menstruum places the microbubbles in a dynamic environment. The height of the aqueous menstruum means that microbubbles in the dispersion will experience different static pressure heads as they travel upwardly through the reactor. Increased pressure will, all else substantially the same, reduce the size of a microbubble. For a given gas feed rate, a greater surface area will be provided by the smaller microbubbles which enhances mass transfer. The size of a microbubble will also be affected by the diffusion of gases from the microbubble to the liquid phase. As carbon monoxide and hydrogen constitute a significant mole fraction of the microbubble as it is introduced into the aqueous menstruum, the dynamic conditions will promote a population of microbubbles that have small diameters to aid in maintaining the gas-in-water dispersion throughout the reactor.

The injectors may be located at one or more locations in the reactor and oriented in any suitable direction. The injectors may be located in a lower portion of the deep, tank reactor. However, an advantage provided by using a deep, MLD tank reactor is that injectors may be placed at two or more heights. Due to the mechanical mixing, the dispersion introduced will be relatively uniform through out the reactor and the average gas residence time will be advantageous to assure the sought transfer of carbon monoxide and hydrogen to the liquid phase. By locating the injectors over the height of the reactor, the uniformity of composition of the gas-in-liquid dispersion in the aqueous menstruum is promoted and less mechanical stirring energy may be required to maintain the sought uniformity.

Pre-Reaction System

The pre-reactor assembly contains at least one pre-reactor. The pre-reactor system serves to reduce the mole fraction of carbon monoxide in the treated gas feed. As the microorganisms are less sensitive to hydrogen oversupply, the processes of this invention need not effect significant hydrogen conversion in the pre-reactor assembly. Given that the mass transfer rate of hydrogen is lower than that of carbon monoxide, the pre-reactor assembly can be sized and operated based upon the targeted carbon monoxide conversion efficiency. The pre-reactor is configured and operated such that carbon monoxide inhibition does not occur in either of the pre-reactor or deep, tank reactor. Accordingly, variables such as maximum static pressure, gas feed bubble size, rate of mixing and culture density should be taken into account in selecting the configuration and operating conditions for a given gas feed composition. As the deep, tank reactor provides the bulk of the gas substrate conversion to oxygenated organic compound, the pre-reactor assembly need not be operated at the edge of product production rate and carbon monoxide inhibition in order to obtain advantageous conversion efficiencies overall.

Although the use of a single pre-reactor is preferred due to capital costs, the processes of this invention contemplate pre-reactor assemblies containing two or more pre-reactors in parallel or in series where performance benefits are obtained. Also contemplated in the broad aspects of the processes of this invention is by-passing a portion of the gas feed such that the gas feed to the deep, tank reactor is at a desired composition. A pre-reactor assembly may be used to provide treated gas feed to more than one deep, tank reactor.

The treated gas feed from the pre-reactor assembly contains from about 5 to 30, preferably from about 10 to 25, mole percent carbon monoxide; from about 10 to 60, preferably about 10 to 50, mole percent hydrogen; from about 10 to 80, mole percent carbon dioxide; about 0 to 20 mole percent nitrogen and from about 0 to 10 mole percent methane. The treated gas feed may contain other components.

The pre-reactor may be of any suitable configuration including, but not limited to, bubble column reactors, especially bubble column reactors having an aqueous menstruum height of less than about 10 meters, preferably less than about 5 meters; jet loop reactors; stirred tank reactors; trickle bed reactors; biofilm reactors; and static mixer reactors including, but not limited to, pipe reactors. For those pre-reactor configurations in which the feed gas is in the form of bubbles in an aqueous menstruum, bubble sizes that are larger than those in the aqueous menstruum of the deep, tank reactor are preferred. These bubble sizes, while reducing the rate of mass transfer and thus conversion of gas substrate, reduce the risk of carbon monoxide inhibition.

Product Recovery:

Product recovery can consist of known equipment arrangements for removal of residual cell material, separation and recovery of liquid products from the fermentation liquid, return of recovered fermentation liquid and purging of waste streams and materials. Suitable equipment arrangement can include filters, distillation columns, membrane systems and other separation equipment. US 2009/0215139 A1 shows an arrangement for a product recovery reactor that recovers an ethanol product from a bioreactor, herein incorporated by reference in its entirely.

DRAWINGS

A general understanding of the invention and its application may be facilitated by reference to FIG. 1. FIG. 1 is a schematic depiction of an apparatus generally designated as 100 suitable for practicing the processes of this invention. FIG. 1 omits minor equipment such as pumps, compressors, valves, instruments and other devices the placement of which and operation thereof are well known to those practiced in chemical engineering. FIG. 1 also omits ancillary unit operations. The process and operation of FIG. 1 will be described in the context of the recovery and production of ethanol. The process is readily adaptable to making other oxygenated products such as acetic acid, butanol, propanol and acetone.

As shown, substrate gas feed is provided to apparatus 100 via line 102. The substrate gas comprises carbon monoxide, hydrogen, carbon dioxide, methane, nitrogen and some trace gases and can be derived from any suitable source. Line 102 feeds the substrate gas feed to pre-reactor 106. Pre-reactor 106 may be of any convenient design that effects back mixing of aqueous menstruum in the reactor. Typical pre-reactor designs include stirred tank reactors, static mixer reactors such as baffled pipe reactors, bubble column reactors and flow mixing reactors where the incoming gas and/or liquid feeds effect agitation of the aqueous menstruum. For purposes of illustration in connection with the drawing, the pre-reactor is a stirred tank reactor. Pre-reactor 106 contains aqueous menstruum. The aqueous menstruum contains microorganisms for the fermentation, water, ethanol product and adjuvants and nutrients for the microorganism. Liquid for the aqueous menstruum is provided by line 104 and may be one or more of recycled liquid fermentation medium, make-up fermentation medium and water.

Pre-reactor 106 is maintained under suitable fermentation conditions to produce ethanol. Advantageously the fermentation conditions including bubble size, pressure, mixing and average residence time of the gas feed pre-reactor 106 is sufficient for the microorganisms to convert between about 10 and 40 mole percent of the carbon monoxide in the substrate gas feed to ethanol. Usually the rate of conversion of carbon monoxide in reactor 106 is greater than that of hydrogen. Due to the low targeted conversion, the volume of the aqueous menstruum in pre-reactor 106 can be relatively small in comparison to the deep, tank reactor 140 to be described later.

Pre-reactor 106 contains an aqueous menstruum having both liquid and gas phases. Reactor 106 has a gas head space (not shown) containing off gas from the aqueous menstruum. These off gases can be withdrawn via line 118. As shown, liquid aqueous menstruum having gas and liquid phases, is withdrawn via line 108 and is directed to either or both of lines 112 and 114 by valve 110. Line 112 directs the mixed phase stream to deep, bubble column fermentation reactor 140. Line 114 directs the mixed phase stream to phase separator 116. In many instances, the pre-reactor assembly will not require phase separator 116 as adequate gas separation occurs in pre-reactor 106.

Preferably aqueous menstruum containing microorganisms from pre-reactor 106 is passed directly to reactor 140 rather than to a phase separator. But where phase separator 116 is used, valve 110 directs at least a portion of the fluid in line 108 to line 114. Phase separator 116 provides a gaseous overhead and a liquid bottoms containing a reduced concentration of carbon monoxide and hydrogen in the gas phase. The gaseous overhead is removed via line 120 and passed to valve 124. Valve 124 is adapted to direct all or a portion of the gaseous overhead to line 126 for processing in carbon dioxide removal device 128. Typically no carbon dioxide removal will be done as the carbon dioxide assists in reducing the mole fraction of carbon monoxide and hydrogen in the gas feed to deep, tank reactor 140. However, carbon dioxide removal can be beneficial in certain circumstances such as the conversion of carbon monoxide in pre-reactor is sufficient that the carbon dioxide dilution in the gas feed is unnecessary to avoid carbon monoxide inhibition. Carbon dioxide removal device 128 may be any suitable device such as amine extraction, alkaline salt extractions, water absorption, membrane separation, adsorptions/desorption, and physical absorption in organic solvents. As shown, carbon dioxide is removed by sorption into an aqueous stream containing ethanol. The sorbent is provided via line 130 and spent sorbent is withdrawn from carbon dioxide removal device 128 via line 132 for regeneration. A treated off gas is produced in carbon dioxide removal device 128 and is withdrawn via line 134 and passed to gas header 138 which directs gas to bubble column fermentation reactor 140.

Valve 124 is also adapted to pass all or a portion of the fluid in line 120 via line 136 to gas header 138. The relative portions passing to line 126 and line 136 will typically be dependent upon the sought carbon dioxide concentration for the gas entering bubble column fermentation reactor 140. For instance, at start-up, it may be desired to have a high carbon dioxide concentration in the gas entering deep, bubble column fermentation reactor 140 in order to maintain a low carbon monoxide partial pressure. Hence a major portion, if not all, of the fluid in line 120 may be passed to line 136. Under steady state operation, a major portion if not all, of the fluid in line 120 may be passed to line 126 provided that the gas fed to reactor 140 has the desired carbon dioxide concentration.

Deep, bubble column fermentation reactor 140 contains liquid fermentation media comprising microorganisms for conversion of substrate gas to ethanol. As discussed above, other types of deep, tank reactors may be used. The treated gas feed from the pre-reactor assembly provided by lines 112 and 138 is supplied to a lower portion of deep, tank reactor 140 via an injector using a motive liquid to form microbubbles. Preferably the microbubbles and aqueous menstruum in deep, tank reactor 140 form a stable dispersion. The microbubbles ultimately pass upwardly from a bottom portion of reactor 140 to an upper portion. The gas emanating from the top of the aqueous menstruum enters a head space at the top of reactor 140 and is withdrawn via line 142. The withdrawn gas is exhausted from the apparatus and may be used for product recovery and heat generation. Aqueous menstruum is withdrawn from an upper portion of reactor 140 and processed to recover ethanol.

Deep, tank reactor 140 is also adapted for recycle. As shown, a portion of the aqueous menstruum in line 144 is withdrawn via line 146. A portion of this withdrawn menstruum can be purged via line 148. The purging serves to prevent a build up of one or more components in the liquid menstruum in reactor 140. Make-up water, nutrients and other adjuvants for the fermentation can be supplied by line 150. Line 146 passes the liquid to valve 160. Valve 160 is adapted to direct all or a portion of the liquid via line 152 for recycle into bubble column fermentation reactor 140. This recycle liquid can be used as motive fluid for the injection of gas into reactor 140 as can the liquid from line 138 and 158 as identified below. Valve 160 is also adapted to direct none or a portion of the liquid into recycle liquid header 162 for passage to back mix reactor 106.

Turning back to phase separator 116, liquid phase is withdrawn via line 122. All or a portion of the liquid can be directed via line 164 for ethanol product recovery. In some instances, all product recovery is from aqueous menstruum contained in deep, tank reactor 140. The remaining portion of fluid in line 122 can be recycled to either or both of pre-reactor 106 and deep, tank reactor 140. Valve 156 controls the flow of liquid in line 122 that passes into line 158 for introduction into deep, tank reactor 140. The remainder, if any, of the liquid is passed to recycle liquid header 162 for admixture with liquid being provided via line 104. Line 104 may also supply make-up water, nutrients and adjuvants for the microorganisms. Adequate make-up water, nutrients and adjuvants may be supplied by the aqueous menstruum in line 162.

It is claimed:

1. A continuous process for the anaerobic bioconversion of a gas substrate comprising carbon monoxide, carbon dioxide and hydrogen in an aqueous menstruum containing microorganisms suitable for converting said substrate to oxygenated organic compound, said process comprising:

a. continuously supplying a gas feed comprising said gas substrate to a pre-reactor assembly comprising at least one pre-reactor and contacting the gas feed with an aqueous menstruum therein, said contacting being under conditions sufficient to convert in the pre-reactor assembly between 10 and 40 percent of carbon monoxide in the gas feed to said oxygenated organic compound and provide a pretreated gas comprising unreacted carbon monoxide in a mole fraction less than that in the gas feed, unreacted hydrogen, and carbon dioxide in a mole fraction greater than that in the gas feed;

b. continuously supplying at least a portion of the pretreated gas to a deep, tank reactor as microbubbles having a diameter of less than 500 microns for contact with an aqueous menstruum therein, said contacting being under conditions sufficient to provide a total, overall molar conversion of carbon monoxide and hydrogen contained in said gas feed in steps a and b to said oxygenated organic compound of at least 80 percent; and c. recovering oxygenated organic compound from the aqueous menstruum from the deep, tank reactor.

2. The process of claim 1 wherein the microbubbles have a diameter of between 10 and 300 microns.

3. The process of claim 1 further comprising passing aqueous menstruum in the pre-reactor system to the deep, tank reactor.

4. The process of claim 1 wherein the pre-reactor system contains a single pre-reactor.

5. The process of claim 1 wherein the pre-reactor system contains at least one continuously stirred tank reactor.

6. The process of claim 1 wherein the pre-reactor system contains at least one bubble column reactor.

7. The process of claim 1 wherein the pre-reactor system contains at least static mixer reactor.

8. The process of claim 1 wherein the pre-reactor system contains at least one jet loop reactor.

9. The process of claim 1 wherein the deep, tank reactor is a continuously stirred tank reactor.

10. The process of claim 1 wherein the deep, tank reactor is a bubble column reactor.

11. The process of claim 1 wherein between 25 and 40 percent of the carbon monoxide contained in the feed gas to the pre-reactor assembly is converted to oxygenated organic compound.

12. The process of claim 11 wherein at least a portion of pretreated gas from the pre-reactor assembly is subjected to process conditions to remove at least a portion of the carbon dioxide therein.

* * * * *